|  |

(12) United States Patent
Treptow

(10) Patent No.: US 7,118,709 B2
(45) Date of Patent: Oct. 10, 2006

(54) METHOD AND APPARATUS FOR TEMPERING SPECIMENS

(75) Inventor: Rainer Treptow, Norderstedt (DE)

(73) Assignee: Eppendorf AG, Hamburg (DE)

( * ) Notice: Subject to any disclaimer, the term of this patent is extended or adjusted under 35 U.S.C. 154(b) by 509 days.

(21) Appl. No.: 10/001,762

(22) Filed: Oct. 31, 2001

(65) Prior Publication Data

US 2002/0055187 A1 May 9, 2002

(30) Foreign Application Priority Data

Nov. 3, 2000 (DE) ............... 100 54 487

(51) Int. Cl.
*B32B 5/02* (2006.01)
(52) U.S. Cl. ............... 422/82.01; 422/82.02; 422/98; 422/102; 436/149; 436/150
(58) Field of Classification Search ........... 422/68.1, 422/82.01, 82.02, 98, 102; 436/149, 150
See application file for complete search history.

(56) References Cited

U.S. PATENT DOCUMENTS

| 4,697,451 | A | * | 10/1987 | Matteson | .............. | 73/64.52 |
| 5,141,868 | A | * | 8/1992 | Shanks et al. | ............ | 435/287.9 |
| 5,284,748 | A | * | 2/1994 | Mroczkowski et al. | ........ | 435/6 |
| 5,287,758 | A | * | 2/1994 | Geiss et al. | .............. | 73/864.01 |
| 5,532,128 | A | * | 7/1996 | Eggers et al. | .................. | 435/6 |
| 6,232,129 | B1 | * | 5/2001 | Wiktor | ...................... | 436/180 |
| 6,267,015 | B1 | * | 7/2001 | Incavo | .................... | 73/863.11 |
| 6,439,068 | B1 | * | 8/2002 | Windolph | .................. | 73/865.5 |
| 6,582,660 | B1 | * | 6/2003 | Heller et al. | ............... | 422/68.1 |
| 6,602,714 | B1 | * | 8/2003 | Tagge et al. | ................... | 436/2 |
| 6,649,357 | B1 | * | 11/2003 | Bryan et al. | ................. | 435/7.1 |
| 6,670,607 | B1 | * | 12/2003 | Wood et al. | ................ | 250/288 |
| 6,680,206 | B1 | * | 1/2004 | McDevitt et al. | .......... | 436/172 |

FOREIGN PATENT DOCUMENTS

| DE | 3132926 | 7/1982 |
| GB | 2333250 | 7/1999 |
| WO | 9824548 | 6/1998 |
| WO | 9857180 | 12/1998 |
| WO | 9961578 | 12/1999 |

\* cited by examiner

*Primary Examiner*—Jill Warden
*Assistant Examiner*—Dwayne K Handy
(74) *Attorney, Agent, or Firm*—Abelman, Frayne Schwab

(57) ABSTRACT

A method for tempering at least one sample wherein an plastic-based electrically conductive material of a specimen carrier consisting at least partially of this material for at least one specimen is applied to by an electric current/an electric voltage which causes a resistance heating of at least one portion of the plastic-based electrically conductive material, which resistance heating heats a specimen disposed on the specimen carrier.

11 Claims, 2 Drawing Sheets

METHOD AND APPARATUS FOR TEMPERING SPECIMENS

Figure 1:
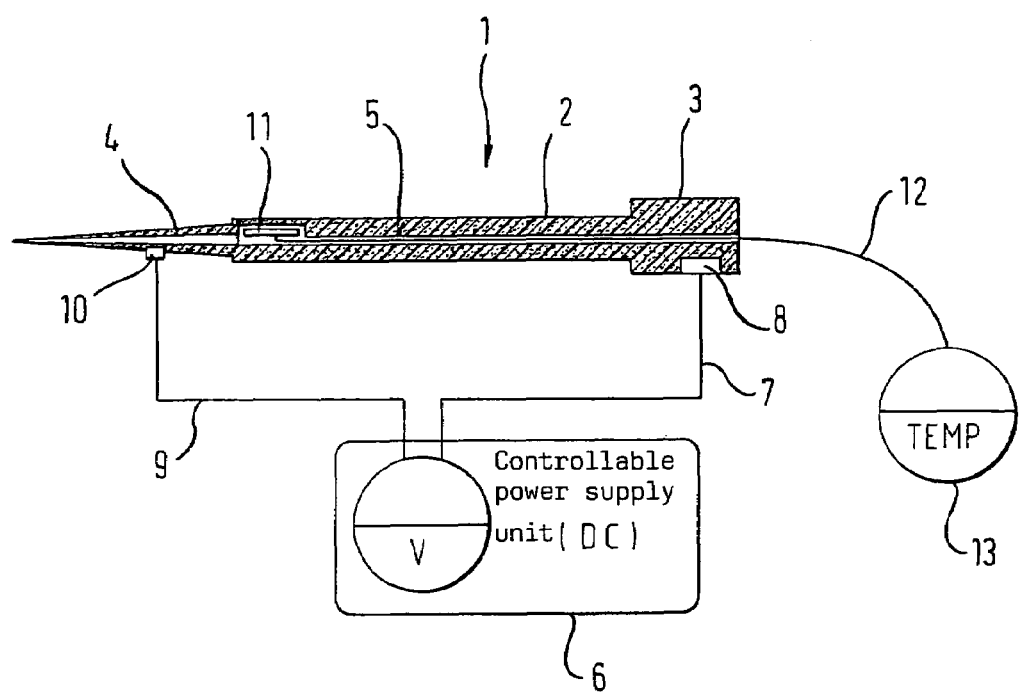

This invention relates to a method and apparatus for tempering specimens.

The method and apparatus are employed, in particular, for tempering specimens at laboratories. The specimens concerned are predominantly liquid specimens. Generally, however, the method and apparatus may also relate to solid or gaseous specimens or multiphase specimens such as suspensions or emulsions.

Specimens of this type are frequently treated, handled or stored in expendable articles at laboratories. Thus, pipette tips or syringes made of plastic material serve for proportioning and transporting specimens. Cuvettes in plastic are resorted to for photometric measurements, but also for tempering in tempering apparatus through which heat is fed to the cuvettes from outside. Accordingly, it has already been known to temper reaction vessels and centrifuge vessels in plastic in tempering apparatus from outside. The same applies to microtitration plates which can be tempered by means of an external incubator or thermostats.

These known tempering techniques have in common that the expendable article which thermally can be considered an insulator, is heated by an enclosure encircling it and that this one is heated by a heating element. Because of these two heat transition points, tempering is comparatively slow, imprecise, not very efficient and expensive, as a rule. However, there is a need to carry out tempering and other treatments in a time-saving and accurate manner within a sequence.

Moreover, a disadvantage in withdrawing a microtitration plate from an external tempering apparatus, for example, is that the temperature will collapse until further use, which can impair the apparatus.

It has been known already to speed up heat transfer in microtitration plates for the PCR by reducing the wall thickness of the material. However, limits are set thereto.

WO 97/26993 has made known a method and apparatus for heating specimens in receptacles of a specimen carrier. The specimen carrier is a metallic plate. It is either designed as a full-walled silver block or a plastic carrier on which a metal layer is deposited. The specimen carrier is heated by resistance heating. Since large currents flow in the metal the document recommends that the specimen carrier be fed from a heavy-duty secondary circuit of a transformer in which the cross-section of the secondary winding is significantly larger than is the cross-section of the specimen carrier so that considerable heat generation only occurs in the specimen carrier. Moreover, the current may be easily controlled via the primary winding, in which the current is small, by means of thyristors, triacs or other devices. Instead, the primary winding can also be operated via a high-frequency switched-mode power supply unit in order to control the current induced in the secondary winding to the same extent. This heating of specimens involves great expenditure in instruments.

Accordingly, it is the object of the invention to provide a method and apparatus which allow specimens to be tempered in a more rapid, more precise, more efficient, and less expensive manner.

The object is achieved by a method having the features of claim 1, and an apparatus having the features of claim 21. Advantageous aspects of the method and apparatus are given in the sub-claims.

In the inventive method for tempering at least one sample, a plastic-based electrically conductive material of a specimen carrier consisting at least partially of this material for at least one specimen is applied to by an electric current and/or an electric voltage which causes a resistance heating of at least one portion of the plastic-based electrically conductive material, which resistance heating heats a specimen disposed on the specimen carrier.

The inventive apparatus for tempering at least one specimen, particularly by performing the aforementioned method, has a specimen carrier made of a plastic-based, at least partially conductive material for at least one specimen, and a device for applying an electric current and/or an electric voltage to the plastic-based electrically conductive material in order to cause a resistance heating of at least some part of the plastic-based electrically conductive material, which heating heats a specimen disposed on the specimen carrier.

Applying an electric current and/or an electric voltage to the plastic-based electrically conductive material causes a resistance heating by which a specimen contained in the receptacle is heated. To this end, it is understood that the plastic-based electrically conductive material has a resistance between the points at which the electric current and/or the electric voltage is applied, the consequence of which is the resistance heating necessary for the heating desired for the specimen. It is particularly the composition of the plastic-based electrically conductive material which allows to vary the resistance in question wherein a very good reproduction of the resistance can be achieved. In contrast to the metallic specimen carrier which is known, the resistance can be chosen so as to require comparatively low currents for the resistance heating. This makes comparatively low the expenditure needed for current and/or voltage supply.

For example, pipette tips made of plastic, which are known already and have become electrically conductive by embedding graphite in the plastic, may be resorted to for the specimen carrier in order to detect immersion into a liquid. Of course, a pipette tip may also be specifically constructed for the realization of the invention.

However, the invention is also suited to temper other specimen carriers which can have a memory volume or memory locations for the specimens. The first group, in particular, includes syringes, cuvettes, reaction vessels, centrifugating vessels or microtitration plates. The second group, in particular, includes test bands or bio-chips.

Test bands have at least one substrate which can be wetted by a specimen in order to furnish a detection by a reaction with the substrate which, for example, can be ascertained by a change in color. Bio-chips have a substrate in silicon, glass or plastic or another material on which a multiplicity of different DNA specimens (e.g. about 1 million) are deposited. These test sequences may be simultaneously checked for their coincidence with the respective sequences of the genotype of a test person in a single operation. A coincidence is there as far as DNA single strands form a double strand (hybridization). The bonding of the DNA marked by means of fluorescent substances to certain target fields on the chip can be automatically recorded by confocal fluorescence microscopy.

The specimen carrier, in particular, can be designed so as to have only one of the above functions. However, it may also combine several functions. Preferably, the specimen carrier is designed as an expendable article. The specimen carrier concerned, however, may also be an article for multiple use.

The invention makes it possible to temper specimens in a rapid and direct way at a low cost. This can be advantageously take place also as a treatment step in a sequence, particularly at a time lag with another treatment process or simultaneously therewith. Thus, for example, tempering and proportioning may be per-formed in a simultaneous, time-lagging or overlapping way in a pipette tip or syringe. Also, tempering is frequently required for spectroscopic measurements in cuvettes. Just here, a material dyed black by carbon has the advantage to provide good protection from stray light. Of course, the light passage points of cuvettes require to be transparent so that transparent materials may be employed here as well. Fluorescence titration plates, however, may be made completely black if a measurement is made here through the upper-side apertures of the receptacles. It may be expected that the optical protective effect of the carbon is even better than the simple black color imparted to the known fluorescence titration plates. In automatic titration plate instruments, temperings and other specimen treatments may be simultaneously made in one or more titration plates.

In addition, the invention permits to continue tempering a specimen even after the specimen is removed from a tempering apparatus as far as the current or voltage supply of the specimen carrier is ensured. This is possible, for example, for pipette tips which are mounted on automatic pipetting machines in order to transfer specimens there. Generally, however, the invention allows to permanently temper pipette tips connected to a hand-held pipette.

The invention also incorporates an application in which the specimen carrier is a device having a contact area to put on and temper another specimen carrier which directly contains the specimen, i.e. the heating surface of a tempering apparatus. This avoids the transfer of heat from a heater winding to the heating surface for a further specimen carrier. It is understood that the further specimen carrier can also be configured as an inventive specimen carrier to support heating in putting the surface on the contact area or to continue it upon removal from the contact area or to maintain the temperature that was reached. According to an advantageous aspect, the specimen carrier can comprise electric contacts and/or electric printed conductors and/or electronic components. The electric contacts may specifically serve the low-resistance defined connection to an electric current and/or voltage source. Electronic components which are considered here are particularly sensors, e.g. those for the temperature, or optical signaling elements such as light-emitting diodes. Printed conductors, in particular, may serve for connecting electric contacts to the plastic-based electrically conductive material and/or connecting the electronic components to each other or the afore-mentioned elements. In particular, if the specimen carrier is designed as a bio-chip it is possible to integrate contacts and/or printed conductors and/or electronic components on the chip. The manufacturing techniques known in the printed-circuit board and chip production may be utilized.

The specimen carrier and/or the device for applying a current and/or a voltage may have one or more temperature measuring devices.

The heating and/or cooling of the specimen may be specifically determined by integrating at least one temperature sensor in the specimen carrier and/or placing at least one temperature sensor in the specimen and/or determining the internal resistance of the plastic-based electrically conductive material of the specimen carrier and/or by at least one optic temperature sensor. For temperature determination, it is also possible to integrate liquid crystals in the specimen carrier, the optical characteristics of which reversibly change if a certain temperature is exceeded so that the crystals will absorb light in different ways.

The plastic-based electrically conductive material concerned, in particular, may be an electrically conductive plastic or an electrically conductive plastic mixture or a material mixture composed of one or more plastic materials and one electrically conductive material. The plastic materials which are considered, in particular, are polyethylene, polypropylene, and polycarbonate alone or in any combination. The electrically conductive material which is considered, in particular, are electrically conductive particles. These may specifically be metallic particles, e.g. aluminum particles. Preferably, however, the particles are carbon, particularly graphite particles or carbon fibres. It is also possible to employ various electrically conductive materials in combination.

In the method and apparatus for tempering, the plastic-based electrically conductive material preferably is an integral part of the specimen carrier. For reasons of manufacture, it may be advantageous if the whole specimen carrier is made of the plastic-based electrically conductive material. Generally, however, the invention merely presupposes at least one wall of the specimen carrier or one portion or layer thereof to be made of the plastic-based electrically conductive material. As was already mentioned above wall portions, e.g. those of cuvettes, may be composed of a particularly transparent material. This can be a material other than an electrically conductive material. It is also possible to provide the electrically conductive material only in one layer of one or more walls of the specimen carrier, e.g. in an outer layer, to avoid impairing a specimen, which contacts an inner layer of the wall, by the electric current.

According to an aspect, the specimen carrier is integrally made of one or more plastic materials. Thus, the specimen carrier may be homogeneously manufactured from a plastic-based electrically conductive material or may consist of this material only in some regions, and of one or more other materials in the remaining regions. The other materials, for example, may be more or less electrically insulating materials (e.g. to separate individually heatable memory locations and/or memory volumes for specimens) and/or light-transmissive materials (e.g. for cuvette windows) and/or material-transmissive materials (e.g. for a diaphragm for materials separation). Expendable articles may be integrally made of plastic material in a particularly inexpensive way. In particular, the specimen carrier may be moulded in a single-component or multi-component injection molding process. The latter applies, in particular, to a design comprising different materials.

Generally, working is feasible with a direct current and/or a direct voltage where, however, it is possible for the specimen to be affected by electrophoretic effects, for example, if the plastic-based electrically conductive material is in a direct contact with the specimen. To specifically avoid this impairment, an alternating current and/or an alternating voltage can be used.

The invention incorporates the option to control the electric current and/or electric voltage which is applied to the electrically conductive material. If the current is constant the heating efficiency may be kept essentially constant in spite of temperature-caused changes in resistance or variable contact resistances. If the current is constant the resistance may increase with an increase in heating, thus causing the current and temperature to decrease. As a result, temperature regulation can be achieved if the temperature steeply rises initially. Also, it may be possible to change over between current-controlled working and voltage-controlled working.

Heating, i.e. a timed and/or local temperature distribution in the specimen located on the specimen carrier, can be acted on in various ways. Reference was already made above to the effect exerted by the composition of the plastic-based electrically conductive material. In addition, it is possible to influence heating via the structure and further composition of the specimen carrier. It is specifically possible via the shape and dimensions of the specimen carrier and the shape and dimensions of specimen carrier zones made of different materials.

In addition, the heating of the specimen can be acted on by applying a certain current and/or a certain course of current and/or a certain voltage and/or a certain course of voltage at certain points of the specimen carrier.

Further, a purposeful influence can be exerted on heating in certain regions of the specimen carrier by the fact that certain currents and/or certain courses of current and/or certain voltages and/or courses of voltage can be applied at several certain points in order to selectively energize different regions of the specimen carrier made of plastic-based electrically conductive material. Thus, if the specimen carrier is designed as a microtitration plate different receptacles of the microtitration plate may be differently tempered. This allows to design a "gradient cycler" in a particularly simple manner.

In a "gradient cycler", specimens may be treated at different temperatures or courses of temperature in the various receptacles of a microtitration plate in order to determine the optimum temperatures. For this purpose, in known embodiments, microtitration plates are inserted in metallic blocks which have Peltier elements for heating and cooling the various regions of the microtitration plate.

The inventive specimen carrier, especially in its embodiment as a microtitration plate, also makes it possible to employ further heating and/or cooling elements for speeding up and/or equalizing heating and/or cooling. Heating and/or cooling elements which are particularly considered are Peltier elements or fans. Since the specimen carrier has a resistance heating Peltier elements may also be used for cooling purposes only, which extends their service life. This is particularly beneficial in realizing a "gradient cycler".

According to an aspect, the volume of the specimen is capacitively measured on the specimen carrier. At this point, the volume of a specimen is determined by the influence which the arrangement of the specimen between the plates has on the capacitance of a capacitor. The measuring principle is set forth, for example, in O. Limann, Elektronik ohne Ballast, $5^{th}$ edition, explanations on FIGS. 15.01 through 15.13. For example, the tempering of the specimen can be controlled more precisely because the volume of the specimen was measured. According to an aspect, the specimen carrier has at least one capacitive measuring sensor which is associated with a memory location and/or a memory volume for a specimen. For a capacitive measurement, the capacitive measuring sensor is connected to a capacitance measuring circuit. The capacitance measuring circuit concerned can be a bridge circuit or H.F. resonance circuit (see Limann, loc. cit., explanations on FIGS. 15.05 through 15.09).

The capacitive measuring sensor may have capacitor plates made of an electrically conductive material (e.g. a metal) which are integrated in the specimen carrier. According to an aspect, the capacitive measuring sensor has capacitor plates formed from a plastic-based electrically conductive material of which the specimen carrier is partially made. This also enables the capacitive measuring sensor to be integrally formed with the specimen carrier. The plastic-based electrically conductive material concerned may specifically be one of the materials which can also be employed for the resistance heating of the specimen. Preferably, the material of the capacitor plates has a conductivity which is far better than that of the material for the resistance heating. It is understood that the specimen carrier has an electrically insulating material between the capacitor plates. The plastic-based electrically conductive material for resistance heating, in turn, may be disposed separately from the capacitor plates.

According to an aspect, the specimen carrier is contacted by means of electrically conductive needles in order to apply the electric current/the electric voltage to the specimen carrier for resistance heating and/or to connect the capacitance measuring circuit to the capacitive measuring sensor. The electrically conductive needles may form part of a needle-bed adapter which has end-positioned contacts which directly contact the plastic-based electrically conductive material and/or contact contacts connected thereto. The end-positioned contact areas may penetrate into the material of the specimen carrier, but need not do so because the variance of the transition resistance is irrelevant. The design of the end-positioned contact areas can be pointed, two-dimensional or crown-like. According to an aspect, the contact surfaces of the specimen carrier are coated with a metal.

The apparatus preferably has an apparatus portion comprising the devices for applying an electric current and/or an electric voltage and/or the capacitance measuring circuit or the needle bed adapter, which apparatus portion can be separated from the specimen carrier. The separable apparatus portion is stationary and/or portable. The apparatus portion concerned may be a pipetting device and/or a proportioning device which can be designed as a hand-held or stationary instrument. For instance, this can be a spectrometer if the specimen container is a cuvette. However, it can also be a device for treating reaction vessels (e.g. a thermo-mixer) and/or for treating centrifuge vessels (e.g. a centrifuge) and/or for treating microtitration plates (e.g. a gradient cycler).

To apply the current and/or the voltage, the specimen carrier and the devices for applying a current and/or a voltage may have electric contacts which ensure a rapid and reproducible electric connection even though the devices for applying a current and/or a voltage are disposed in a separable device portion. According to an aspect, respective contacts may exist to connect the capacitive measuring sensor to the capacitance measuring circuit. As was stated above the electric contacts comprise a needle bed adapter.

The device for applying a current and/or a voltage can have a direct-current and/or alternating-current and/or voltage source.

In addition, the device for applying a current and/or a voltage may comprise a device for controlling the heating of the specimen. The invention will now be described in more detail with reference to the accompanying drawings of embodiments which show a pipette tip and some part of a microtitration plate in a roughly diagrammatical way.

According to FIG. 1, an electrically conductive pipette 1 in polypropylene with embedded graphite particles has a cylindrical shank 2 with a fastening portion 3 at one end and a conically tapering tip portion 4 at the other end. In the pipette tip, an axial passage 5 which opens into the two ends and serves for receiving liquid and an air cushion to displace the liquid extends through the pipette tip.

A controllable direct-current power supply unit 6 is connected to a contact 8 on the fastening portion 3 via a line 7 and to a contact 10 on the tip shank 4 via a line 9. For testing purposes, the contacts are realized with conductive varnish. Copper is preferably the appropriate material for mass production. Large-surface contacting is generally advantageous to avoid contact resistances.

A temperature sensor 11 is introduced into the passage of the pipette tip 1 through the aperture on the fastening portion 3 and is connected to a temperature measuring device 13 outside the pipette tip 1 via a line 12.

To make measurements, an electrically conductive pipette tip 1 of the applicant is used, which has been used hitherto merely to detect the liquid level. The tip used has a capacity of 1,100 μl and a resistance of less than 30 kiloohms.

It was found out that a stable temperature of abt. 42° C. adjusts itself in the passage 5 if there is a controlled voltage of 70 V D.C.

A temperature of abt. 70° C. adjusts itself in the passage 5 if there is a voltage of 80 V D.C.

The temperature gradient as measured by applying a voltage of 80 V D.C. is abt.:

10° C. within 30 seconds

30° C. within 90 seconds

If the temperature is increased by 20° C. the resistance will increase by abt. 1.5 kiloohms.

It is possible to reduce the voltage for heating, particularly by varying the carbon proportion of the material of the pipette tip 1 and its geometry.

Figure 2:
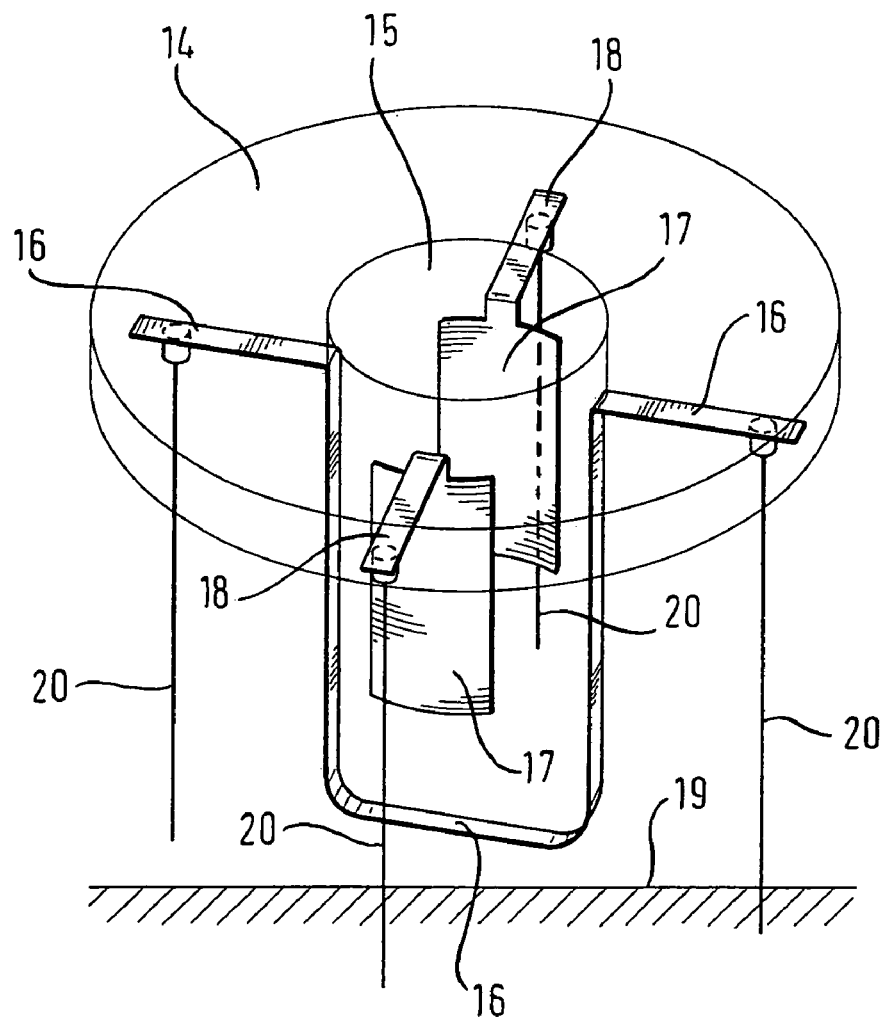

FIG. 2 shows a portion of a microtitration plate 14 which has a strip-shaped web 16 of plastic-based electrically conductive material extending across the underside of the receptacle 15 and adjoining planar portions of the microtitration plate 14 in the range of an indentation 15 for receiving a specimen liquid.

The underside of the receptacle 15 further has capacitor plates 17 on diametrically opposed sides of the receptacle 15, which are aligned perpendicularly to the web 16. The capacitor plates 17 also are made of a plastic-based electrically conductive material (but may also be formed by integrated metallic plates) and are connected to webs 18 made of a plastic-based electrically conductive material (or metallic bands) which are disposed in the adjoining planar regions of the underside of the microtitration 14.

There is an electrically insulating material between the web 16 and the capacitor plates 17 and the webs 18. Respective webs 16, 18 and capacitor plates 17 also exist on further receptacles 15 of the microtitration plate 14 which are not illustrated in the drawing. The webs 16, 18 of adjoining webs 15 are also electrically insulated from each other.

The webs 16, 18 are contacted via a needle-bed adapter 19 having a multiplicity of parallel-aligned, upstanding needles 20. The needle-bed adapter passes an electric voltage/an electric current into the web 16 to effect resistance heating. Further, the needle-bed adapter connects a capacitance measuring circuit to the capacitor plates 17 via the webs 18. This enables a specimen in the receptacle 15 to be tempered and the filling level of the specimen to be determined in the receptacle 15. The filling level, in turn, may be utilized for controlling the tempering operation or for other purposes.

The invention claimed is:

1. A method for tempering at least one specimen, wherein a plastic-based electrically conductive material of a specimen carrier (1, 14) consisting at least partially of this material for at least one specimen is applied to by an electric current/an electric voltage which causes a resistance heating of at least one portion of the plastic-based electrically conductive material, which resistance heating heats a specimen disposed on the specimen carrier (1, 14), wherein a volume of the specimen is capacitively measured on the specimen carrier, wherein at least one capacitive measuring sensor (17) of the specimen carrier (14) which is associated with a memory location and/or a volume( 15) for a specimen and is connected to a capacitance measuring circuit for a capacitive measurement, and wherein the at least one capacitive measuring senor (17) has capacitator plates formed by the plastic-based electrically conductive material of which the specimen carrier (14) is partially made are connected to the capacitance measuring circuit for a capacitive measurement.

2. A method for tempering at least one specimen, wherein a plastic-based electrically conductive material of a specimen carrier (1, 14) consisting at least partially of this material for at least one specimen is applied to by an electric current/an electric voltage which causes a resistance heating of at least one portion of the plastic-based electrically conductive material, which resistance heating heats a specimen disposed on the specimen carrier (1, 14), and wherein the specimen (14) is contacted by means of electrically conductive needles (20) in order to apply the electric current/the electric voltage to the specimen carrier (14) for resistance heating and/or to connect the capacitance measuring circuit to the capacitive measuring sensor (17).

3. A apparatus for tempering at least one specimen, comprising a microtitration plate made of plastic-based, at least partially electrically conductive material for at least one specimen, and a device for applying an electric current and/or electric voltage to the plastic-based electrically conductive material in order to cause a resistance heating of at least some part of the plastic-based electrically conductive material, which heating heats a specimen disposed on the microtitration plate wherein the device for applying an electric current and/or an electric voltage, and a capacitance measuring circuit are adapted to be connected to the microtitration plate via a needle bed adapter (19).

4. The apparatus according to claim 3, wherein the microtitration plate has a web defining a memory location and/or memory volume for the specimen and made of the plastic-based electrically conductive material.

5. The apparatus according to claim 3, comprising portion which comprises the device for applying an electric current and/or an electric voltage and/or the capacitance measuring circuit and/or the needle bed adapter (19) and is separable from the microtitration plate.

6. The apparatus according to claim 5, wherein the separable apparatus portion is stationary and/or portable.

7. The apparatus according to claim 5, wherein the separable apparatus portion comprises a proportioning device, and/or spectrometer, and/or device for treating microtitration plates.

8. The apparatus according to claim 3, wherein the device for applying an electric current and/or electric voltage has a direct-current source and/or an alternating-current source and/or a direct voltage and/or an alternating-current source.

9. The apparatus according to claim 3, wherein the device for applying an electric current and/or an electric voltage have one or more temperature measuring devices.

10. The apparatus according to claim 3, wherein the device for applying an electric current and/or electric voltage has a device for controlling the heating of the specimen.

11. The apparatus for tempering at least one specimen comprising:
- a microtitration plate made of plastic-based, at least partially electrically conductive material for at least one specimen, and
- a device for applying an electric current and/or electric voltage to the plastic-based electrically conductive material in order to cause a resistance heating of at least some part of the plastic-based electrically conductive material, which heating heats a specimen disposed on the microtitration plate, wherein the microtitration plate has at least one capacitive measuring sensor (17) associated with a memory location and/or memory volume (15) for a specimen to measure the volume of at least one specimen, and a capacitance measuring circuit connected to the capacitive measuring sensor (17).

wherein the capacitive measuring sensor has capacitor plates (17) which are formed of a same material of which the microtitration plate is partially made, wherein the specimen carrier and the devices (6,7,9) for applying an electric and/or an electric voltage and/or the capacitance measuring circuit have electric contacts via which electric current and/or electric voltage can be applied to the specimen carrier and/or is adapted to be connected to the capacitive measuring sensor (17) via the capacitance measuring circuit.

* * * * *